United States Patent [19]

Enjolras et al.

[11] Patent Number: 5,091,193
[45] Date of Patent: Feb. 25, 1992

[54] DIAPER RASH TREATMENT AND COMPOSITIONS

[75] Inventors: Odile Enjolras, Meudon; Hugues Noel, Ermont, both of France

[73] Assignee: Roussel Uclaf, France

[21] Appl. No.: 570,224

[22] Filed: Aug. 21, 1990

[30] Foreign Application Priority Data

Aug. 23, 1989 [FR] France .................. 89 11172

[51] Int. Cl.$^5$ .................................... A61K 33/32
[52] U.S. Cl. .................................... 424/642; 514/143; 514/865
[58] Field of Search ............... 514/147, 494, 865, 143; 424/642

[56] References Cited

U.S. PATENT DOCUMENTS 4,556,560 12/1985 Buckingham ............ 424/145
4,857,321 8/1989 Thomas ..................... 424/95

OTHER PUBLICATIONS

Chemical Abstracts 88:65874 (1978).

*Primary Examiner*—Leonard Schenkman
*Attorney, Agent, or Firm*—Bierman and Muserlian

[57] ABSTRACT

A composition for preventing or treating diaper rash comprising an effective amount of zinc oxide and at least one antienzyme sufficient to treat or prevent diaper rash and an inert pharmaceutical carrier and a method of treating or preventing diaper rash on newborn babies.

10 Claims, No Drawings

DIAPER RASH TREATMENT AND COMPOSITIONS

STATE OF THE ART

Water pastes are dermopharmaceutical preparations based on zinc oxide which encourages healing and are intended to treat irritations caused by the maceration of stools and urine in the diapers of new-born babies The structure of the skin of the new-born baby much resembles the skin of an adult if the infant is full-term, but premature babies have a corium which does not yet totally fulfill its function as a barrier. Normally, the pH of the skin is acid, from 4 to 5.5 and the skin is able to counter and endure external attack in children as in adults.

But in new-born babies, diapers can create a more hostile environment than that usually encountered by the skin, increasing the risk of dermatitis where the dermis is attacked and the skin is irritated and inflamed.

The principal cause of the irritation which characterizes diaper dermatitis or diaper rash is the mixture of urine and stools. In effect, the urea contained in the urine is broken down into ammonium hydroxide by the ureases which leads to an increase in pH. When the pH becomes basic, the enzymes produced at time of digestion such as the proteases and the lipases of pancreatic or intestinal origin, see their activity and thus their irritating power increase. The lipases in particular attack the triglycerides of the sebum and provoke the release of fatty acids.

The corium made permeable by a hyperhydration, a significant rubbing and digestion by enzymes loses its function as a barrier and allows other irritating molecules such as biliary salts to pass through. In certain cases, an actual digestion of the epidermis of the infant's bottom could be observed due to the action of ureases, lipases and proteases.

To combat diaper rash, the means used in current therapy such as supervision of the infant's diet and the type of diaper used and ensuring good hygiene and the application of standard barrier creams are not judged satisfactory by a large number of dermatologists and pediatricians.

Pertinent prior art includes U.S. Pat. No. 1,809,082, soap, perfumery and cosmetics, Vol. 54 No. 11 (Nov. 1981) and Chem. Abs., Vol. 93 No. 16 (1980), p. 355, No. 155864d.

OBJECTS OF THE INVENTION

It is an object of the invention to protect new-babies against diaper rash and to provide novel anti-diaper rash compositions.

These and other objects and advantages of the invention will become obvious from the following detailed description.

THE INVENTION

The novel compositions of the invention a for preventing or treating diaper rash are comprised of an effective amount of zinc oxide and at least one anti-enzyme sufficient to treat or prevent diaper rash and an inert pharmaceutical carrier.

The combination of anti-enzymes in a barrier cream facilitates the irritations caused by stools to be treated and considerably diminishes the lipolytic, proteolytic and ureasic actions causing the irritation. Preferably, the compositions contain zinc oxide and one or more anti-enzymes which are enzyme inhibitors whose method of working can be of various types. An example of inhibition is that caused by chelating agents which restrict the metals which are indispensable to the activity of the enzyme.

Among the chelating agents useful are phytic acid but also useful are nitrilotriacetic acid, ethylene diamino tetracetic acid, diethylene triamino pentacetic acid and hydroxyethyl ethylene diamino triacetic acid as well as the corresponding acid salts. These chelating agents can be used preferably at a concentration of 0.1 to 2%.

These compositions are particularly intended for the treatment of diaper rashes in new-born babies and have a curative and preventing double action. The anti-enzymes are chosen from antilipases, anti-proteases and anti-ureases and the compositions of the invention can contain one or more anti-enzymes from one, two or three of the enzymatic categories indicated.

A preferred group of compositions of the invention contain an antilipase which is an ester of a fatty alcohol such as disclosed in U.S. Pat. No. 2,305,172. These esters of a fatty alcohol may be, for example, saturated or unsaturated, linear or branched, alkyl acetate, lactate or propionate containing 10 to 20 carbon atoms, preferably at a concentration of 0.1 to 5%.

Another preferred group of compositions of the invention are those in which phytic acid is used as an anti-urease or at least one anti-proteases of the group consisting of a) phytic acid, b) a saturated or unsaturated, linear or branched zinc salt of a fatty acid of 2 to 22 carbon atoms, c) a zinc salt of an aminated acylated acid of the formula $$R_1-CO-NH-R_2 \qquad I$$

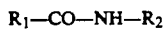

wherein $R_1-CO-$ is an acyl derived from a saturated or unsaturated, linear or branched fatty acid of 2 to 22 carbon $-NH-R_2$ is derived from a natural aminated acid or a protein hydrolysate.

Examples of zinc salts of a saturated or unsaturated, linear or branched fatty acid of 2 to 22 carbon atoms are those formed with propionic acid, isobutyric acid, caproic acid and undecylenic acid.

Examples of zinc salts of an aminated acylated acid of formula I are $R_1CO$ derived from propionic acid, butyric acid, caproic acid, undecylenic acid or palmitic acid, and $-NH-R_2$ is either a radical derived from a natural aminated acid chosen from glycine, alanine, valine, leucine, isoleucine, serine, threonine, cystein, methionine, lysine, arginine, aspartic acid, glutamic acid, phenylalanine, tyrosine, histidine, proline and ornithine, or a radical derived from a protein hydrolysate such as, for example, collagen, gelatin, silk, keratin, wool, feather or horse hair, soya, wheat (gluten) or corn.

Examples of zinc salts of an aminated acylated acid of the formula $$R_1-CO-NH-R_2$$

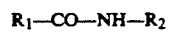

are propionylcysteine, propionyl-hydroxyproline or caproylcysteine (LIFACIDE ®).

Preferably, the anti-protease chosen is phytic acid also used as anti-urease. The preferred concentration of phytic acid is between 0.1 and 2% in the preparations as defined above.

The pharmaceutical compositions of the invention can have all the forms used in dermatology, preferably in a manner capable of being administered locally: solutions, emulsions, creams, ointments, powders, milks, conditioning lotions or gels, according to the type, in pots or tubes, in glass or plastic bottles or possibly in measuring bottles or also in ampoules.

For each form, appropriate excipients are used which must have all the qualities usually required. In the case of a local administration, they must be endowed with a strong affinity for the skin, be perfectly well tolerated, stable and show an adequate consistency to allow their easy and agreeable use.

Examples of excipients are polymers of a carboxyvinyl type, polyethyleneglycols, propyleneglycol, waxes, fatty substances, esters and triglycerides of fatty substances, stearic derivatives such as, for example, glycerol stearate, alcohols such as, for example, stearyl alcohol, ketostearyl alcohol, ketyl alcohol, polyol, polyoxyethylene ketyl ether, vegetable oils such as soft almond oil, mineral oils such as vaseline oil, glycerin, derivatives of lanolin, talc, wetting agents, thickening agents, stabilizing agents, emulsifying agents, preservatives, perfumes, colorants or other known and currently used excipients.

The cosmetic compositions can be prepared by using the same ingredients and the dosages can be adapted, if necessary. The preferred forms are the pharmaceutical compositions defined above characterized in that they are presented in the form of a gel or cream.

Also a subject of the invention is the cosmetic compositions to treat diaper rash in new-born babies characterized in that they contain zinc oxide and one or more anti-enzymes.

The novel method of the invention for the treatment or prevention of diaper rash in new-born babies comprises applying an amount of a composition of the invention to the skin of new-born babies sufficient to treat or prevent diaper rash.

In the following examples there are described several preferred embodiments to illustrate the invention. However, it should be understood that the invention is not intended to be limited to the specific embodiments.

EXAMPLE 1

A diaper barrier cream was prepared consisting of the following ingredients.

| Ingredient | Amount |
|---|---|
| Zinc oxide | 20 |
| Titanium oxide | 3 |
| Talc | 10 |
| Hectorite | 1 |
| Aluminium silicate | 5 |
| Silica | 2 |
| Hydroxyethylcellulose | 0.5 |
| Polyglycol | 10 |
| Glycerin | 15 |
| 1,3 Butanediol | 5 |
| D panthenol | 2 |
| Oleyl acetate | 1 |
| Phytic acid | 1 |
| Propionyl hydroxyproline | 1 |
| Caproylcystein | 1 |
| Collegen amino acid palmitate | 0.5 |
| Water | sqf 100 |

EXAMPLE 2

A diaper barrier cream was prepared consisting of the following ingredients:

| Ingredient | Amount |
|---|---|
| Zinc oxide | 15 |
| Titanium oxide | 3 |
| Talc | 10 |
| Ammonium silicate | 7 |
| Silica | 2.5 |
| Hydroxyethylcellulose | 0.2 |
| Polyglycol | 10 |
| Glycerin | 15 |
| 1,3 Butanediol | 2 |
| D panthenol | 2 |
| Oleyl acetate | 1 |
| Phytic acid | 1 |
| Caprilyc acid and cysteine condensate | 1 |
| Palmitic acid and casein condensate | 0.3 |
| Preservatives | s.q. |
| Water | s.q. for 100 |

Anti-urease activity test, in vitro, of phytic acid

The operating conditions common to the four experiments conducted in parallel, these being 1), 2), 3) and 4), the results of which are shown in the table below, were a mixture of substrate or urea at 0.17 mole/l. and of enzyme or urease at 2 mg/ml (MERK ®) maintained at 30° C. in a thermostatic bath.

Experiment 1) was conducted in the absence of inhibitor while experiments 2), 3) and 4) were carried out in the presence respectively of: for 2) thiourea at 0.17 mole/l, an inhibitor specific to urease, for 3) phytic acid at 0.425 mole/l in 3a) and 0.425 mmole/l in 3b) and for 4) the barrier cream of Example 1.

The table of results below shows that in comparing experiments and 3), phytic acid was a better inhibitor than thiourea. In comparing experiments 3), 3a) and 3b), phytic acid was active at the weak dose of 0.425 mmole/l and in comparing experiments 3b) and experiment 4) where the quantity of phytic acid in the barrier cream was about 0.425 mmole/l, the barrier cream constituted an excellent inhibitor ensuring good stability of pH.

| Time | (1) No inhibitor | (2) Thiourea 0.17 m/l | (3) Phytic acid (3a) | (3) Phytic acid (3b) | (4) Barrier Cream |
|---|---|---|---|---|---|
| 5 s | 6.17 | 6.25 | 6.08 | 6.13 | 6.68 |
| 10 s | 6.68 | 6.76 | — | 6.15 | — |
| 20 s | 7.77 | 7.85 | — | 6.15 | — |
| 40 s | 8.30 | 8.31 | — | 6.15 | — |
| 1 mn | 8.40 | 8.41 | 6.08 | — | 6.68 |
| 2 mn | 8.52 | 8.54 | 6.08 | 6.17 | 6.67 |
| 3 mn | 8.57 | 8.58 | 6.08 | 6.18 | 6.68 |
| 4 mn | 8.60 | — | 6.08 | 6.20 | 6.70 |

Various modifications of the compositions and method of the invention may be made without departing from the spirit or scope thereof and it is to be understood that the invention is intended to be limited only as defined in the appended claims.

What we claim is:

1. A composition for preventing or treating diaper rash comprising an effective amount of zinc oxide, phytic acid, an optional additional anti-enzyme sufficient to treat or prevent diaper rash and an inert pharmaceutical carrier.

2. A composition of claim 1 containing as the optional anti-enzyme an anti-lipase which is an ester of a fatty alcohol.

3. The composition of claim 2 wherein the ester is oleyl acetate.

4. A composition of claim 1 in the form of a cream or gel.

5. A composition of claim 1 containing an additional anti-enzyme.

6. A method of treating or preventing diaper rash in new-born babies comprising applying to the skin of new-born babies an amount of a composition of claim 1 is sufficient to prevent or treat diaper rash.

7. A method of claim 6 containing as anti-enzyme an antilipase which is an ester of a fatty alcohol.

8. A method of claim 6 in the form of a cream or gel.

9. A method of claim 6 containing an additional anti-enzyme.

10. The method of claim 6 wherein the ester is oleyl acetate.

* * * * *